United States Patent [19]

Shimizu et al.

[11] Patent Number: 4,734,528

[45] Date of Patent: Mar. 29, 1988

[54] METHOD FOR PREPARING 3-ETHYLBENZOPHENONE

[75] Inventors: Isoo Shimizu; Yasuo Matsumura, both of Yokohama; Atsushi Sato, Tokyo, all of Japan

[73] Assignee: Nippon Petrochemicals Co., Ltd., Tokyo, Japan

[21] Appl. No.: 904,473

[22] Filed: Sep. 8, 1986

[30] Foreign Application Priority Data

Sep. 11, 1985 [JP] Japan .................................. 60-200809

[51] Int. Cl.$^4$ ............................................. C07C 45/28
[52] U.S. Cl. .................................... 568/309; 568/321; 585/459
[58] Field of Search ................. 568/321, 309; 585/459

[56] References Cited

U.S. PATENT DOCUMENTS 3,898,288 8/1975 d'Ostrowick et al. ............... 568/321
4,086,277 8/1978 Onopchenko et al. .............. 568/309

Primary Examiner—James H. Reamer
Attorney, Agent, or Firm—Fisher, Christen & Sabol

[57] ABSTRACT

The present invention provides a method for preparing 3-ethylbenzophenone in a high purity which comprises the steps of alkylating benzene with ethylene in the presence of an alkylating catalyst to obtain an alkylated product composed mainly of unreacted benzene, ethylbenzene, polyethylbenzenes and heavier substances; subjecting the alkylated product to rectification in order to recover therefrom a fraction which has a temperature range of boiling points within the range of 275° to 310° C. (in terms of atmospheric pressure); heating the recovered fraction together with a mixture of nitric acid and water; carrying out purification, if necessary; and performing distillation to recover therefrom 3-ethylbenzophenone represented by the formula (I):

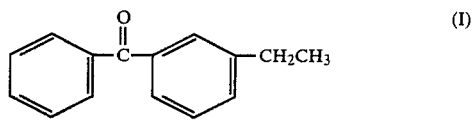

8 Claims, No Drawings

METHOD FOR PREPARING 3-ETHYLBENZOPHENONE

BACKGROUND OF THE INVENTION (i) Field of the Invention

The present invention relates to a method for preparing 3-ethylbenzophenone represented by the formula (I) which is important as a material for the synthesis of medicines and Ketoprofen (trade name):

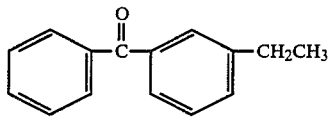

(ii) Description of the Prior Art

As a method for preparing 3-ethylbenzophenone, there is known, for example, a method in which a Friedel-Crafts alkylation is carried out by the use of benzophenone and diethyl sulfate in the presence of aluminum chloride in order to obtain the desired 3-ethylbenzophenone (Spanish Pat. No. 452500). In this Spanish patent, it is also disclosed that a ketoprofen which is a kind of medicine is synthesized from this 3-ethylbenzophenone. However, this method of Spanish patent results in the formation of various by-products, though high-purity raw materials are employed therein. Consequently, in the Spanish patent, the purification of the desired product is difficult and its yield is low.

SUMMARY OF THE INVENTION

An object of the present invention is to provide a method for synthesizing high-purity 3-ethylbenzophenone from specific materials at a low cost.

The present invention is connected with a method for synthesizing high-purity 3-ethylbenzophenone at a low cost. In brief, the method of the present invention comprises alkylating benzene with ethylene in the presence of an alkylating catalyst, distilling the resultant by-products to recover a fraction which has a temperature range of boiling points of 275° to 310° C. (in terms of atmospheric pressure), and oxidizing the recovered fraction by the use of nitric acid and water in order to prepare high-purity 3-ethylbenzophenone (hereinafter referred to simply as EBP).

The material of the present invention is a by-produced oil, that is, a mixture of various compounds chemical structures of which are not known, and thus it has not been employed yet as a material for a chemical reaction.

DESCRIPTION OF THE PREFERRED EMBODIMENTS

For the purpose of preparing a styrene monomer for a polystyrene by dehydrogenation of ethylbenzene, it has been extensively carried out on an industrial scale that benzene is alkylated with ethylene to form ethylbenzene.

In the preparation of ethylbenzene, benzene is first alkylated with ethylene in the presence of an alkylating catalyst in order to prepare an alkylated product mainly comprising unreacted benzene, ethylbenzene, polyethylbenzenes and heavier substances. In this case, a known method for preparing ethylbenzene such as a liquid phase alkylation method or a gaseous phase alkylation method may be utilized. A practical molar ratio of benzene to ethylene can be within the range of about 25:1 to 2:1, preferably about 10:1 to 3:1. In the liquid phase reaction, usable examples of the alkylating catalysts include Friedel-Crafts catalysts such as aluminum chloride, aluminum bromide and organic aluminum halides; Lewis acids such as $ZnCl_2$, $FeCl_3$ and $BF_3$ to which a promotor is added; and Brönsted acids such as sulfuric acid, sulfonic acid and p-toluenesulfonic acid. The above mentioned alkylating catalyst may be employed in an amount of about 0.002 to 0.050 part by weight, preferably about 0.005 to 0.030 part by weight based on the weight of the produced ethylbenzene, and benzene may be reacted with ethylene within the temperature range of about 0° to 175° C., preferably about 20° to 150° C. When the reaction temperature is less than 0° C., the yield of ethylbenzene will deteriorate, and when it is more than 175° C., the yield of ethylbenzene will also drop inconveniently owing to side reactions. With regard to a reaction pressure, a high pressure is preferable because of facilitating the dissolution of ethylene, but the pressures up to 100 kg/cm² are applicable and practicable. A suitable reaction time is usually within the range of about 10 minutes to 10 hours, preferably about 20 minutes to 3 hours.

In the gaseous phase alkylation method, for example, the reactants may be caused to stream over a suitable alkylating catalyst in which phosphoric acid is incorporated into diatomaceous earth, silica, alumina or aluminum silicate, at a temperature within the range of about 250° to 450° C., preferably about 300° to 400° C. at a pressure within the range of about 28 to 85 kg/cm², preferably about 42 to 70 kg/cm² at an ordinary space rate.

As a result of such a reaction, there is prepared an alkylated product mainly consisting of unreacted benzene, the desired ethylbenzene, polyethylbenzenes and heavier substances. If necessary, the alkylating catalyst mixedly present in the alkylated product may be removed therefrom. When, e.g., aluminum chloride is used as the alkylating catalyst, the alkylated product may be delivered to a settling tank, in which the used aluminum chloride catalyst may be precipitated and removed therefrom. If necessary, the removed catalyst may be recycled through and reused in the reaction system. On the other hand, the remaining alkylated product is washed with water and then neutralized.

Next, distillation is carried out to recover a fraction which has a temperature range of boiling points of 275° to 310° C. (in terms of atmospheric pressure), from the alkylated product mainly consisting of unreacted benzene, ethylbenzene, polyethylbenzenes and heavier substances.

In this recovery process, the alkylated product is distilled under a normal pressure to a reduced pressure to distill away unreacted benzene (boiling point 80° C.), ethylbenzene (boiling point 136° C.) and polyethylbenzenes (boiling points 176° to 250° C.) and to thereby obtain the heavier substances, and the latter are further distilled, whereby the material fraction of the present invention can be procured. Alternatively, the direct distillation of the alkylated product is also possible, and it permits preparing the desired material fraction of the present invention. Either recovery process can be selected.

The distillation can be preferably carried out under a reduced pressure of 100 mmHg or less by the use of one or plural towers in each of which the number of theoretical separation plates is 5 or more, preferably 10 or more.

According to such a distillation, there can be recovered a fraction (hereinafter referred to as the material fraction) which has a temperature range of boiling points within the range of 275° to 310° C. (in terms of atmospheric pressure), from the above mentioned alkylated product. When the fraction having a boiling point of more than 310° C. is used, the EBP which is the desired object will be poor in purity and its yield will also deteriorate unpreferably. In consequence, it is important to take care so that the material fraction of the present invention may not substantially contain the components having the boiling points more than 310° C. Inversely, when the components having the boiling points of less than 275° C. are contained therein, the yield of the EBP which is the object of the present invention will go down disadvantageously.

The material fraction of the present invention contains 1,1-(3-ethylphenyl)phenylethane (hereinafter referred to as EPEA) a boiling point of which is not known yet. Even if the boiling point of the material fraction is found and known, the latter will be naturally different from a multi-component system in a fractional temperature in the distillation. It has been confirmed by the inventors of the present application that 1,1-(2-ethylphenyl)phenylethane which is an ortho-isomer of the EPEA is extremely close to the EPEA in the boiling point, and thus its separation from the EPEA by the rectification is absolutely impossible. For this reason, the incorporation of the orth-isomer into the material must be avoided to the utmost, but the present invention is advantageous and convenient, because the material fraction of the present invention contains no ortho-isomer. Further, it has also been confirmed that 1,1-(4-ethylphenyl)phenylethane which is the para-isomer of the EPEA has a boiling point in the vicinity of that of the EPEA.

Therefore, it is possible that an operation is made so as to prevent the material fraction of the present invention from containing the para-isomer, though being difficult. However, even if the fraction containing the para-isomer is used as the starting material fraction of the invention, the desired EBP can be obtained in a high purity according to the method of the present invention. In consequence, the para-isomer which is hard to treat as described above may be contained in the material fraction of the present invention. This is an advantageous point of the present invention.

Moreover, the material fraction of the present invention contains, in addition to the EPEA, many complicated hydrocarbon compounds such as polyalkylbenzenes the boiling points of which are extremely near to that of the EPEA. With regard to these compounds, it is difficult to elucidate their correct chemical structures, and their kinds and compositions are not constant in the material fraction, since they are by-products. It should also be noted that these compounds are absolutely difficult to separate therefrom. The reason why the aforesaid material fraction has not been utilized heretofore as a raw material of a chemical reaction is that the fraction is composed of extremely numerous kinds of compounds.

Next, water and nitric acid, i.e., water-containing nitric acid are added to the material fraction of the present invention thus obtained, followed by heating.

A weight ratio of nitric acid (as 100% nitric acid) to the material fraction of the present invention is required to be 0.03:1 to 3:1, preferably 0.1:1 to 2:1. When an amount of nitric acid is smaller than the aforesaid range, the reaction will not make progess sufficiently, and inversely when it is larger than the range, side reactions will occur. Therefore, both the cases are unpreferable.

Further, it is desirable that a weight ratio of nitric acid (as 100% nitric acid) to water is within the range of 1:20 to 1:1. When water is more than the aforesaid range, the reaction will be hard to advance; when it is less than the range, by-products will be large. In consequence, both the cases are unpreferable.

A reaction temperature is within the range of 30 to 150° C. At a reaction temperature less than 30° C., the reaction will not make progress, and on the other hand, at a reaction temperature in excess of 150° C., any high-purity EBP will not be obtained because of side reactions. Accordingly, both the cases are improper.

A pressure may be applied to the reaction phase at such a degree that the above phase remains in the state of the liquid phase.

Further, a reaction time between nitric acid and water is not particularly limited and can be selected within the range of 1 to several tens hours.

After the reaction under heating, the reaction phase is allowed to stand, whereby an oil layer is separated from a water layer (containing nitric acid), and the latter is then removed therefrom, thereby separating a mixture of nitric acid and water from a reaction mixture.

Afterward, if necessary, purification may be carried out to remove nitro compounds which are by-products in the reaction with nitric acid, and distillation follows to recover the high-purity EPA.

As purifying means for removing the nitro compounds, there are several methods, and any one can be employed. For example, if necessary, an organic solvent such as methanol, ethyl acetate or tetrahydrofuran may be added to the reaction mixture, and heating may be then carried out at a temperature of about 140° to 300° C., preferably 160° to 225° C. for a period of about 10 minutes to 3 hours in order to thermally decompose the nitro compounds which are impurities. The thermally decomposed nitro compounds can be easily separated and removed therefrom by such an operation as distillation. Therefore, the EBP can be recovered in a high purity by means of distillation. In addition, when hydrogenation is carried out at a temperature of room temperature to 150° C. under a pressure of atmospheric pressure to 50 $kg/cm^2$ in the presence of a hydrogenating catalyst such as palladium or nickel in order to reduce nitro groups in the nitro compounds to amino groups, followed by distillation, the high-purity EBP can be recovered. Moreover, as another manner, when the reaction mixture is washed with an aqueous solution of a basic compound such as sodium hydroxide, potassium hydroxide, calcium hydroxide or ammonium, followed by distillation, the EBP can be recovered in a high purity.

The distillation after the reaction with nitric acid or after the purification, if the purification is carried out, is usually accomplished under a reduced pressure, but the latter is not particularly limited.

In this distillation process, if the EBP is recovered as the fraction within the boiling range of more than 310° C. and not more than 340° C. (in terms of atmospheric pressure), preferably 320° to 333° C., the high-purity EBP can be prepared.

Further, even if the para-isomer of the EPEA is contained in the material fraction of the present invention, oxides obtained therefrom can easily be separated by the distillation operation of recovering the fraction containing the aforesaid EBP, and as a result thereof, the high-purity EPB can be obtained.

As described above in detail, the material fraction of the present invention is the specific fraction produced from the alkylation of benzene with ethylene, and thus the desired EBP can be prepared at a very low cost. Further, since the fraction prepared by the specific manufacturing method is used as the starting material, there can be obtained the high-purity EBP containing no ortho- and para-isomers.

Since the material fraction of the present invention contains many hydrocarbons chemical structures of which are not known, it cannot be presumed how these components behave in certain reactions. In addition, these components having unknown structures cannot be separated in fact even by the technique of rectification.

However, in view of the fact that the reaction with water-containing nitric acid in the present invention permits preparing the high-purity EBP, it can be supposed that the structurally unknown components in the material fraction scarcely take part in the reaction with water-containing nitric acid or, even if take part in the reaction, they are converted into other compounds which will be separated out by the subsequent distillation. Therefore, according to the reaction of the present invention, the high-purity EBP can be obtained from the specific fraction containing many components the chemical structures of which are not known and which cannot be separated out even by the distillation.

Now, the present invention will be described in detail in reference to examples, but the latter do not intend to limit the scope of the present invention.

EXAMPLE 1

In a reactor, benzene was brought into contact with ethylene with stirring in a molar ratio of benzene:ethylene being 9:1 in the presence of aluminum chloride at a temperature of 130° C. at a pressure of 4.9 kg/cm$^2$ for 1 hour in a liquid phase. One hour sufficed for the conversion of ethylene all. An amount of used aluminum chloride was 0.0034 part by weight based on ethylbenzene produced. As a result of the analysis of the resultant alkylated product, it was found that there existed therein 49.0% by weight of benzene, 32.9% by weight of ethylbenzene, 17.5% by weight of polyethylbenzenes and 0.5% by weight of heavier substances. The alkylated product was then distilled to recover unreacted benzene, ethylbenzene and polyethylbenzenes, so that heavier substances were obtained in an amount of 0.014 part by weight based on ethylbenzene produced. These heavier substances were further subjected to distillation in order to procure a fraction having a boiling point of 280° to 310° C. (in terms of atmospheric pressure), and the procured fraction was then analyzed by means of GC. It was found from the analytical results that the fraction was composed of 76% by weight of the EPEA, 6% by weight of the EPEA p-isomer and the remainder consisting of polyalkylbenzenes and various other hydrocarbons.

The above mentioned rectification was carried out under a reduced pressure of 5 mmHg, the number of theoretical separation plates being 15.

From the above mentioned material fraction, the EPEA itself could be analyzed anyway in accordance with the GC analysis using capillary columns. However, the EPEA alone could not be separated from the other components present in the above mentioned material fraction even by the rectification, since the other components have boiling points close to or equal to that of the EPEA.

Next, 124 g of the thus obtained material fraction and 400 g of 13% water-containing nitric acid were placed in an autoclave, and heating was carried out with stirring at 100° C. for 8 hours. After the completion of the reaction, the reaction solution was cooled and transferred to a separatory funnel, and a water layer containing nitric acid was then separated therefrom. The oil layer was analyzed by means of GC and it was found that there existed 55% by weight of the EBP, 8% by weight of the unreacted EPEA, 18% by weight of impurities such as polyalkylbenzene or the like and 19% by weight of impurities which would be considered to be nitro compounds.

For purification, the above mentioned oil layer was thermally decomposed at 170° C., and a reduced pressure distillation is then carried out to procure 60 g of a fraction of 320° to 333° C. (in terms of atmospheric pressure). The results of the GC analysis indicated that the purity of the EBP was 95%. Further, it was confirmed that the orthoand para-isomers of the EBP were scarcely contained therein. Incidentally, the identification of the EBP was achieved on the basis of a standard sample of the EBP which had been synthesized separately.

Next, ketoprofen was synthesized in accordance with the above mentioned Spanish patent.

(1) Synthesis of 3-(1-bromoethyl)benzophenone

Into a 200 ml reactor equipped with a reflux condenser and a stirrer, 60 ml of carbon tetrachloride and 10 g of the above mentioned fraction containing 3-ethylbenzophenone were introduced. While stirring the resultant mixture at room temperature, 8.6 g of N-bromosuccinimide and 0.14 g of benzoyl peroxide were added thereto, and reflux was perfomed for 8 hours while stirring the reaction solution. After the reaction solution had been cooled to room temperature, the succinimide was filtered out, and carbon tetrachloride was distilled off from a filtrate under a reduced pressure. The spectrum data of the obtained product were in accord with those of 3-(1-bromoethyl)benzophenone.

(2) Synthesis of 3-(1-hydroxvethyl)benzophenone

In an autoclave, 100 ml of water and 3.3 g of calcium carbonate and 10 g of 3-(1-bromoethyl)benzophenone were placed, and were then heated at 120° C. for 6 hours. The resultant reaction solution was extracted with benzene, and a formed benzene layer was then dried with anhydrous sodium sulfate, followed by distilling off the solvent. The resultant product had the spectrum data which were identical with those of 3-(1-hydroxyethyl)benzophenone.

(3) Synthesis of Ketoprofen

In 50 ml of anhydrous ethanol containing 1.5% of hydrogen chloride, 10 g of 3-(1-hydroxyethyl)benzophenone was dissolved, and an anhydrous ethanol solution containing 0.1 g of [P(CH$_3$)$_3$]PdCl$_2$ was then added thereto. This solution was introduced into an autoclave and was then heated at 95° C. at 500 atms for 5 hours in an atmosphere of carbon monoxide. The reaction solution was then transferred to a 200 ml reactor equipped with a reflux condenser and a stirrer, and 5 ml of concentrated hydrochloric acid was added thereto. Afterward, reflux was carried out for 4 hours in a nitrogen atmosphere. Water was then added to the reaction solution, and extraction was performed by the use of ether. The resultant ether layer was washed with water and was then extracted with a 5% aqueous potassium hydroxide solution. After a water layer had been acidified with hydrochloric acid, extraction was performed by the utilization of ether again. The ether layer was then washed with water and dried with anhydrous sodium sulfate, and ether was distilled off under a reduced pressure. The desired α-(3-benzoylphenyl)propionic acid [Ketoprofen (trade name)] was obtained by its recrystallization from benzene/petroleum ether. Spectra and a melting point of the thus obtained Ketoprofen were the same as those of its authentic sample.

EXAMPLE 2

The procedure of Example 1 was repeated to obtain a material fraction having a boiling point of 290° to 305° C. (in terms of atmospheric pressure) which was composed of the EPEA and the remainder consisting of polyalkylbenzenes and many other hydrocarbons, and 125 g of this fraction and 400 g of 20% nitric acid were placed in an autoclave. Then, heating was carried out with stirring at 80° C. for 8 hours. After the completion of the reaction, the reaction solution was cooled and transferred to a separatory funnel, and a water layer was separated therefrom. The oil layer was analyzed by means of GC and it was found that there existed 60% by weight of the EBP, 9% by weight of the unreacted EPEA, 17% by weight of impurities such as polyalkylbenzene and 14% by weight of impurities which would be considered to be nitro compounds.

Next, for purification, the aforesaid oil layer was dissolved in 100 ml of ethanol, and 1 g of a 5% palladium-activated carbon was added thereto. In an atuoclave, hydrogenation was then carried out at a temperature of 60° C. under a pressure of 5 kg/cm² in the presence of hydrogen until hydrogen was not absorbed thereby any more. The used catalyst was removed from the reaction mixture, and a reduced pressure distillation was then accomplished to obtain 65 g of a fraction of 320 to 333° C. to 310° C. (in terms of atmospheric pressure). As a result of the GC analysis, it was found that the purity of the EBP was 97%. Furthermore, the ortho-isomer and the para-isomer of the EBP were scarcely contained therein.

What is claimed is:

1. A method for preparing 3-ethylbenzophenone in a high purity which consists essentially of the steps of alkylating benzene with ethylene in the presence of an alkylating catalyst comprising aluminum chloride and at a temperature within the range of about 0° C. to 175° C. to obtain an alkylated product composed mainly of unreacted benzene, ethylbenzene, polyethylbenzene and heavier substances; subjecting said alkylated product to distillation in order to recover therefrom a fraction which has a boiling point temperature with the range of 275° C. to 310° C. (in terms of atmospheric pressure); heating said recovered fraction together with a mixture of nitric acid and water at a temperature within the range of about 30° C. to 150° C., said weight ratio of 100% nitric acid to water being within the range of 1:20 to 1:1, and said weight ratio of nitric acid (as 100% acid) to said fraction being with the range of 0.03:1 to 3:1 to produce 3-ethylbenzophenone, and performing distillation to recover therefrom 3-ethylbenzophenone represented by the formula (1):

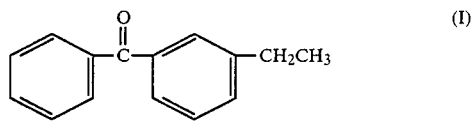

2. A method according to claim 1 wherein nitro-compounds are removed from said 3-ethylbenzophenone product stream prior to distillation.

3. A method according to claim 1 wherein said weight ratio of nitric acid (100% nitric acid) to said fraction is within the range of 0.01:1 to 2:1.

4. A method according to claim 2 wherein said nitro-compounds are removed by thermal decomposition thereof.

5. A method according to claim 2 wherein said nitro-compounds are removed through hydrogenation thereof.

6. A method according to claim 2 wherein said nitro-compounds are removed through washing with a basic aqueous solution.

7. A method according to claim 1 wherein said distillation to recover therefrom 3-ethylbenzophenone is carried out at a temperature with the range of 310° C. to 340° C. (in terms of atmospheric pressure).

8. A method according to claim 7 wherein said distillation is carried out at a temperature within the range of 320° C. to 333° C. (in terms of atmospheric pressure).